United States Patent [19]

Kraft et al.

[11] 4,018,743

[45] Apr. 19, 1977

[54] PROCESS FOR PREPARING TRIKETOIMIDAZOLIDINES

[75] Inventors: Kurt Kraft, Wiesbaden-Dotzheim; Johannes Reese, Wiesbaden-Biebrich, both of Germany

[73] Assignee: Hoechst Aktiengesellschaft, Frankfurt, Germany

[22] Filed: Feb. 28, 1975

[21] Appl. No.: 554,019

Related U.S. Application Data

[63] Continuation of Ser. No. 154,634, June 18, 1971, abandoned.

[30] Foreign Application Priority Data

June 19, 1970 Germany ............................ 2030233

[52] U.S. Cl. ..................... 260/77.5 CH; 260/309.5
[51] Int. Cl.² ......................................... C08G 18/00
[58] Field of Search ................. 260/77.5 CH, 309.5

[56] References Cited

UNITED STATES PATENTS 3,609,113  9/1971  Schade et al. ............. 260/77.5 CH Primary Examiner—M. J. Welsh
Attorney, Agent, or Firm—Littlepage, Quaintance, Murphy & Dobyns

[57] ABSTRACT

A modified N,N'-substituted 2,4,5-triketoimidazolidine containing polycarboxylic acid amide or imide groups at least in the main chain, a process for its manufacture which comprises reacting at a temperature of from minus 20 to plus 280° C (a) at least one oxamidic ester having the group —NH—CO—CO—OR$^v$, wherein R$^v$ is an aliphatic hydrocarbon group having up to 18 carbon atoms, a cycloaliphatic hydrocarbon group with up to 8 carbon atoms, a mononuclear aromatic hydrocarbon group which may contain at least one hydrocarbon group which constitutes a total of up to 14 carbon atoms (b) at least one isocyanate having or yielding 1 to 4 isocyanate groups or isocyanates forming compound and (c) a polybasic carboxylic acid component having 4 to 71 carbon atoms and 2 to 6 carboxylic groups so as to obtain a condensation product possessing amide or imide groups.

23 Claims, 10 Drawing Figures

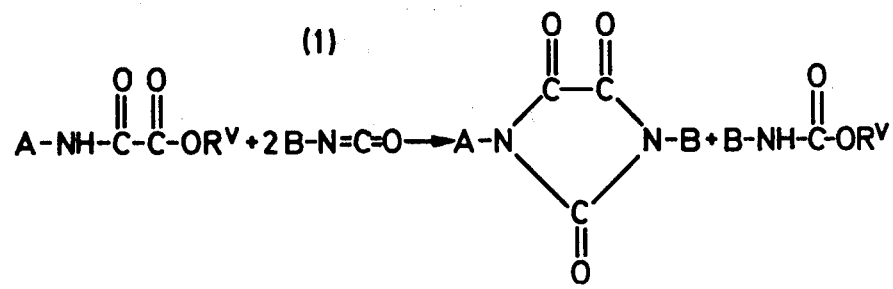
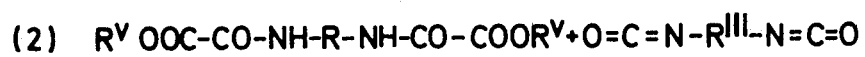
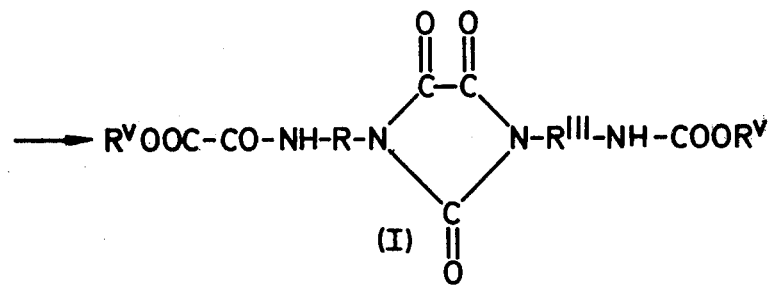
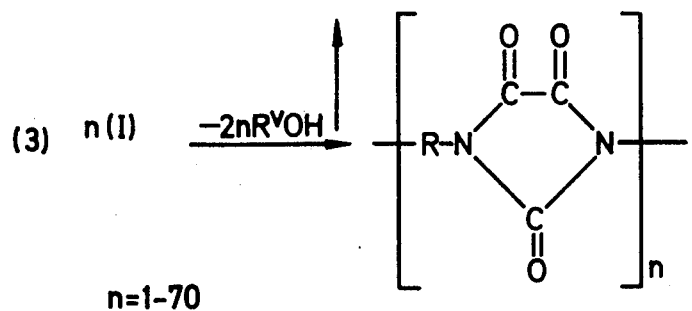

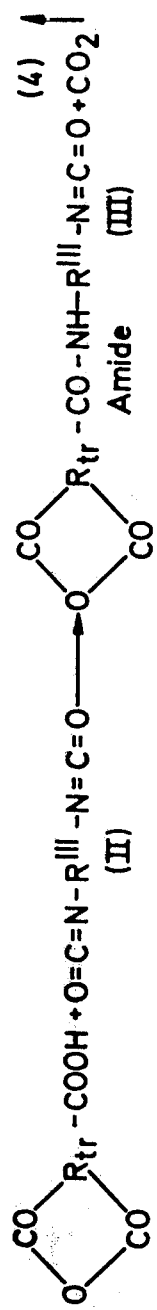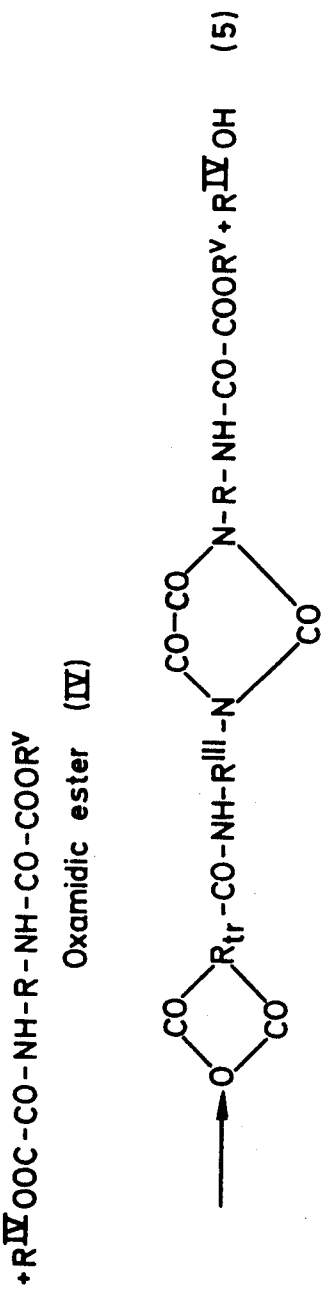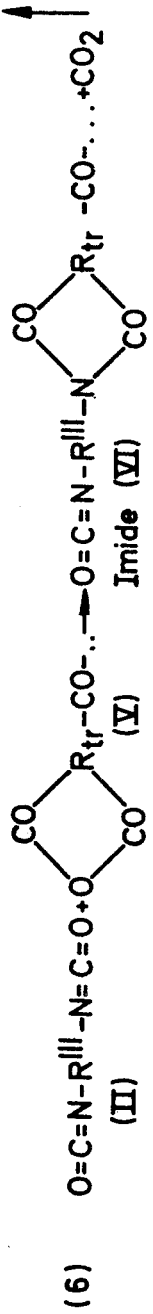

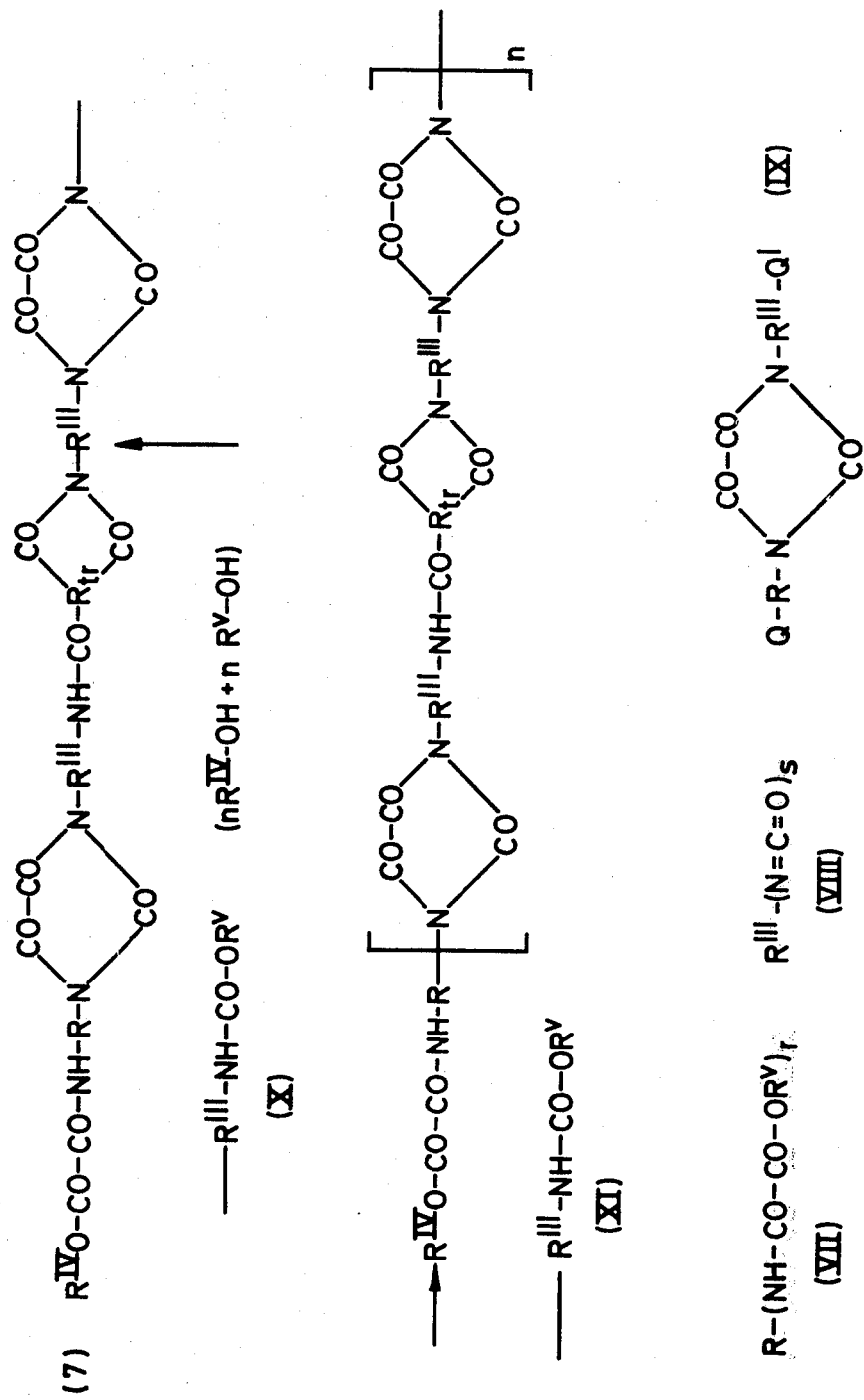

(XII)
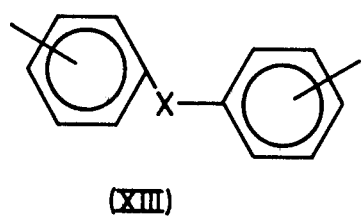
(XIII)
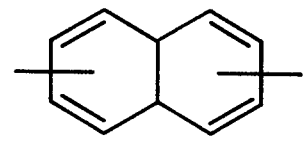
(XIV)
(XV)
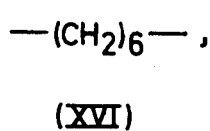
(XVI)
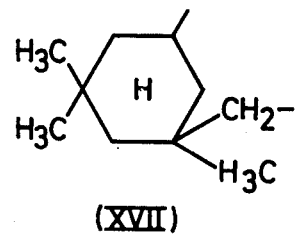
(XVII)
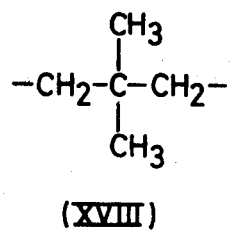
(XVIII)
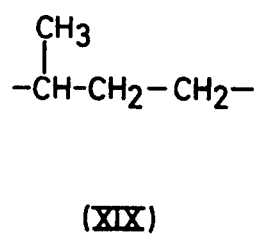
(XIX)

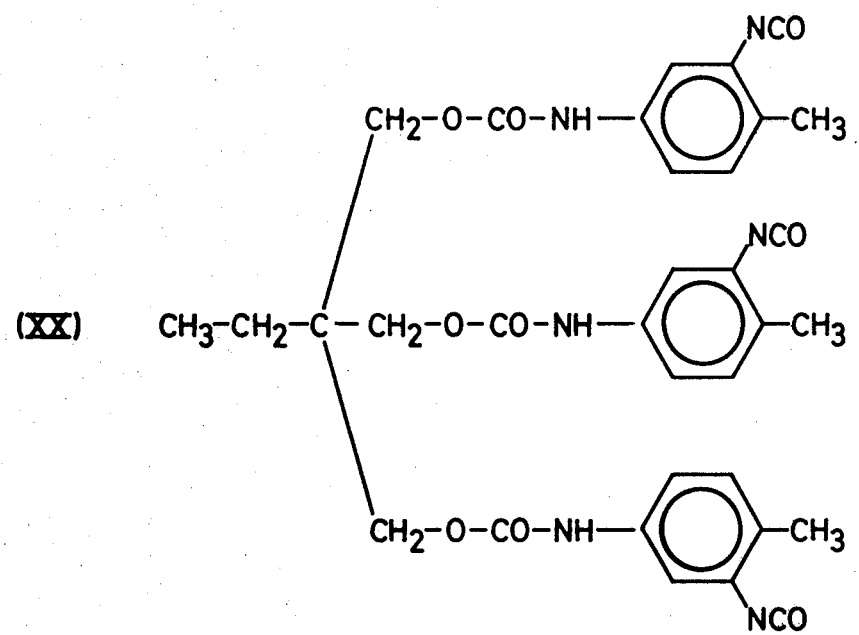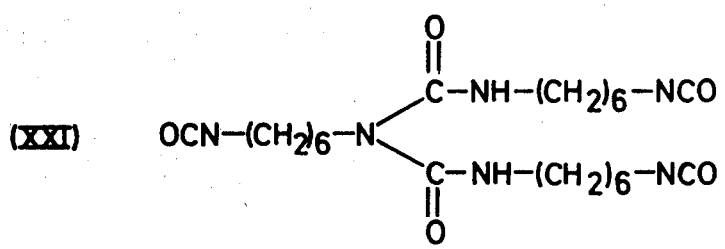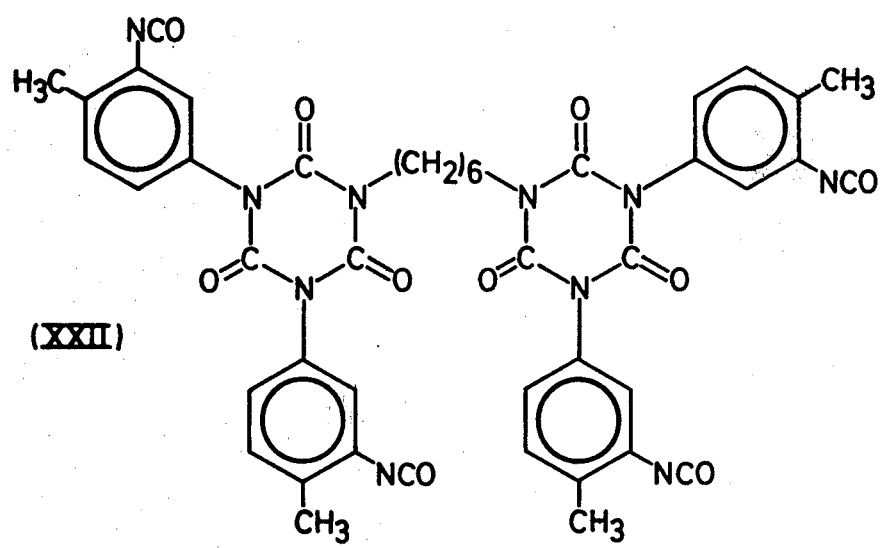

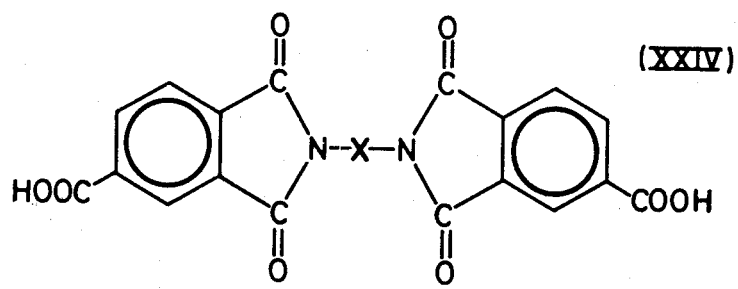
(XXIV)
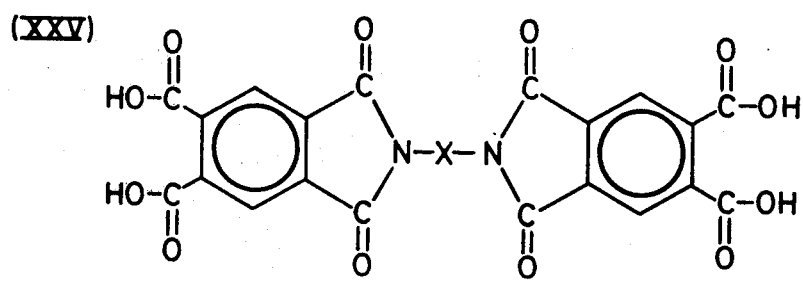
(XXV)
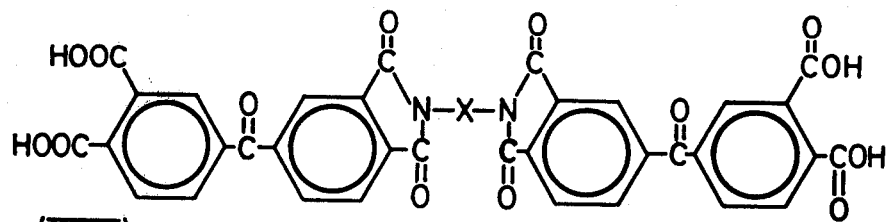
(XXVI)
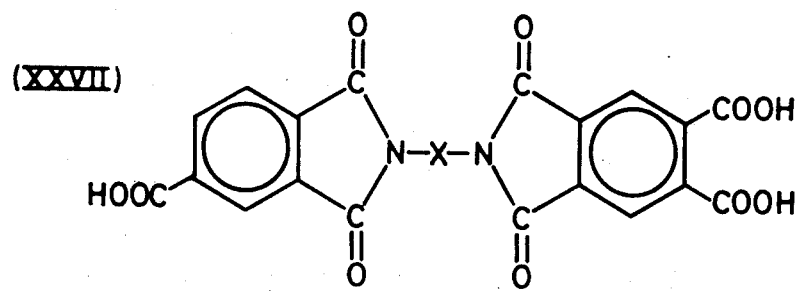
(XXVII)
$X = (CH_2)_m$, $m = 2-8$

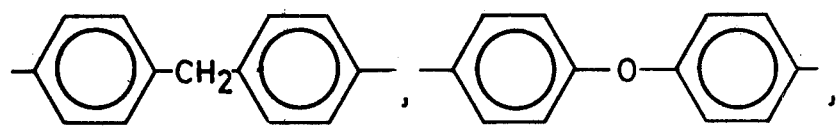
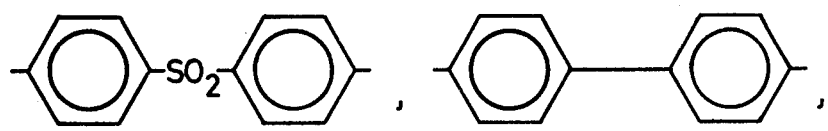
(XXVIIa)
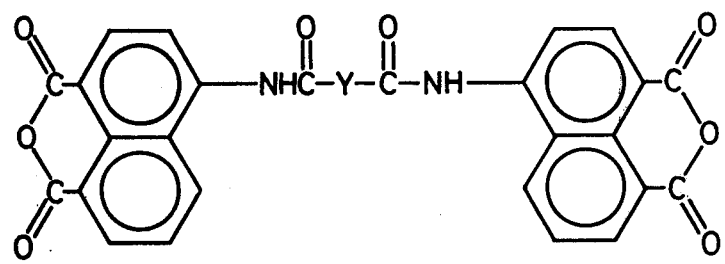
(XXVIII)
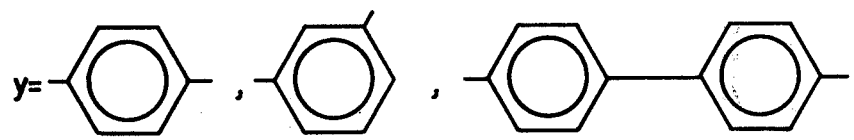
$= (CH_2)_p$   $p = 2-8$   (XXVIIIa)

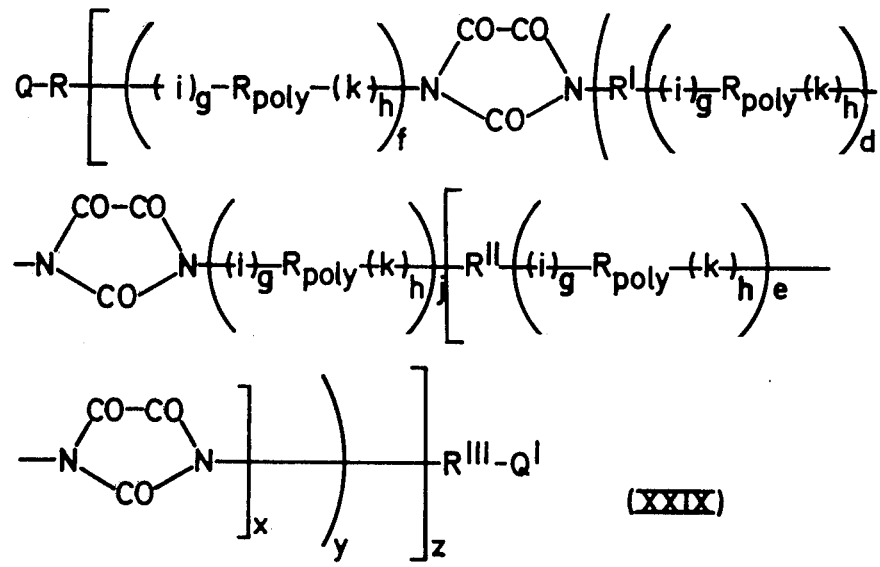
(XXIX)
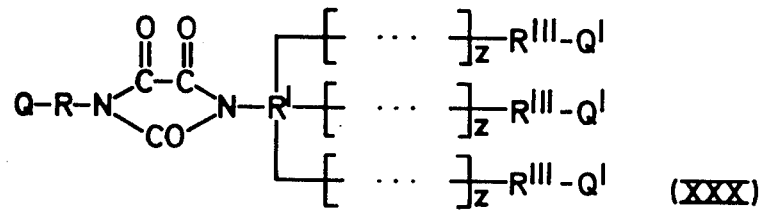
(XXX)
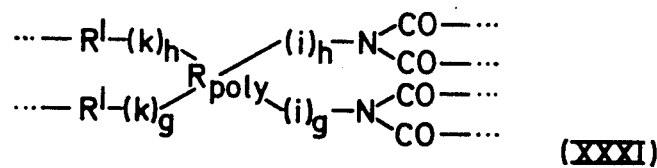
(XXXI)
$$H_2C = (C_6H_5-NH-CO-COOC_2H_5)_2$$
(XXXII)

(8)
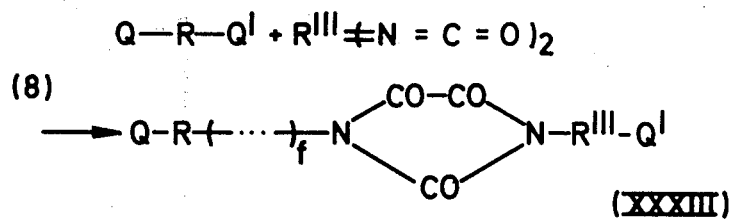
(XXXIII)
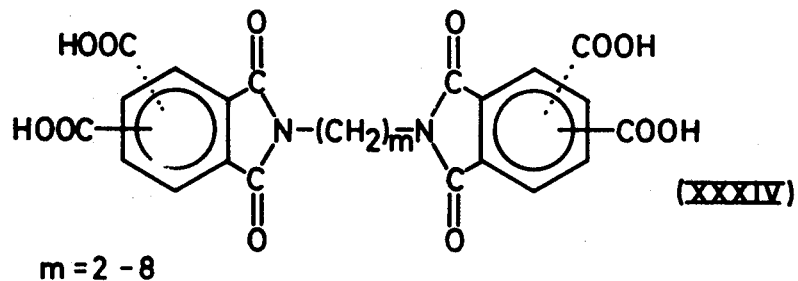
m = 2 – 8
(XXXIV)
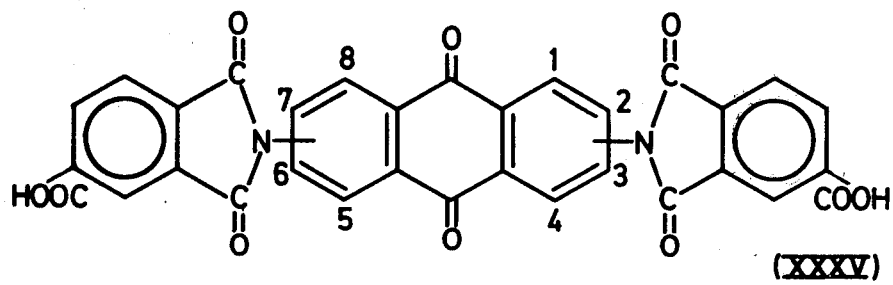
(XXXV)
(9)
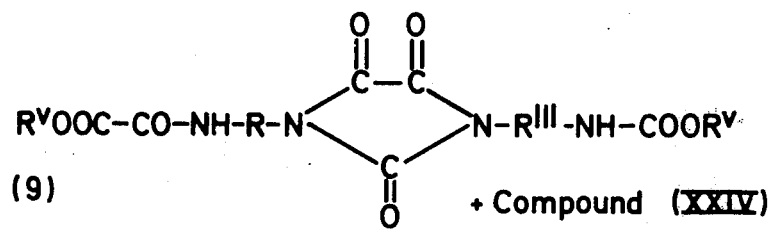
+ Compound (XXIV)

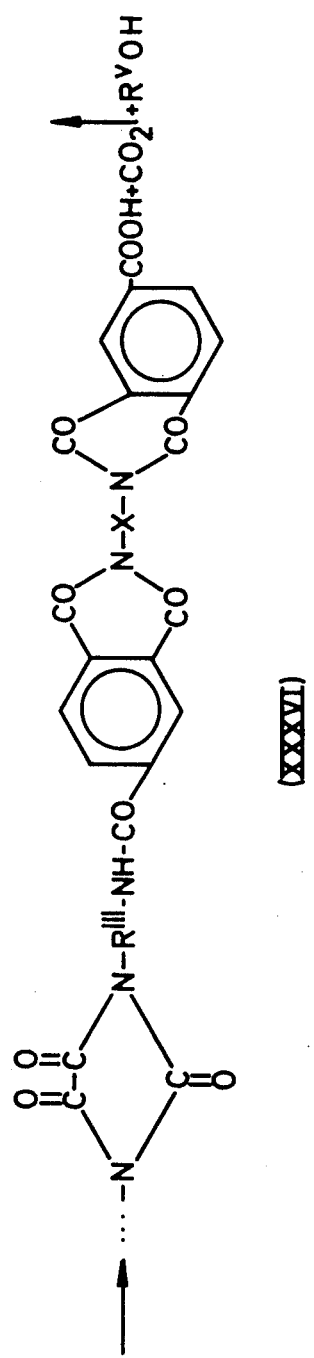

PROCESS FOR PREPARING TRIKETOIMIDAZOLIDINES

This is a continuation of application Ser. No. 154,634, filed June 18, 1971, which is now abandoned.

This invention relates to a process for the preparation of modified N,N'-substituted 2,4,5-triketoimidazolidines.

N,N'-substituted 2,4,5-triketoimidazolidines may be prepared by reacting an alkyl ester of oxamidic acid with an isocyanate. The reaction proceeds according to equation (1) of the accompanying drawings, the second molecule of isocyanate serving as condensation agent in the formation of the imidazolidine ring. This reaction is particularly useful in the preparation of pre-condensates containing terminal groups which can react with one another e.g. according to equation (2) of the drawings.

The terminal groups —NH—CO—COOR$^v$ can react together according to equation (3) with the elimination of two molecules of alcohol so as to form poly-2,4,5-triketoimidazolidine under the influence of heat. It has already been proposed that this type of reaction is of more general application.

In equations (2) and (3):

R is a mono- or polynuclear group which is illustrated in said equations as being only divalent, however, it may also be a mono- to hexavalent carbocyclic or heterocyclic aromatic groups with up to 20 carbon atoms which may be substituted by halogen, nitro, dialkylamino, diarylamino, alkylarylamino, alkyl, alkoxy, carboxyalkyl, carboxyaryl, acyl e.g. acetyl, cycloalkyl or halogenated derivatives of any of alkyl, alkoxy, carboxyalkyl, carboxyaryl, acyl e.g. acetyl or cycloalkyl groups said substituents having up to 18 carbon atoms provided that the aromatic group can also be a quinone if R is connected to an oxamidate radical or no ester groups at all and further provided that polyvalent aromatic groups can be connected to an aliphatic group by at least one hetero atom.

R''' has the meaning given for R and in addition may be an aliphatic hydrocarbon group with 1 to 20 carbon atoms or a cycloaliphatic hydrocarbon group with 5 to 12 carbon atoms.

Pre-condensates containing triketoimidazolidine rings obtained according to equation (3) generally have a relatively low molecular weight. These compounds have proved satisfactory in many ways. However for certain applications compounds with a higher molecular weight are desired and also to improve their handling.

The invention provides a process whereby 2,4,5-triketoimidazolidines of high molecular weight may be obtained. In our process a polybasic carboxylic acid is employed in addition to the oxamidic acid alkyl ester and the isocyanate so that there is formed a material which, in addition to possessing the desired 2,4,5-triketoimidazolidine groups also possesses amido, imido and amidoimido linkages.

Accordingly the invention provides a process for the manufacture of modified N,N'-substituted 2,4,5-triketoimidazolidines which comprises reaction (a) one or more oxamidic esters having the group —NH—CO—CO—OR$^v$, wherein R$^v$ is an aliphatic hydrocarbon group having up to 18 carbon atoms, a cycloaliphatic hydrocarbon group with up to 8 carbon atoms, a mono-nuclear aromatic hydrocarbon group which may be substituted by one or more hydrocarbon groups having a total of up to 14 carbon atoms (b) one or more isocyanates or isocyanate forming compounds and (c) a polybasic carboxylic acid component having 4 to 71 carbon atoms and 2 to 6 carboxylic groups so as to obtain a condensation product possessing amide or imide groups.

When the group R$^v$ is an aliphatic hydrocarbon group it preferably has up to 6 carbon atoms. The polybasic carboxylic acid component may be an acid or an anhydride of the free acid. Furthermore this component has at least 2 and preferably at most 4 carboxylic groups. The process may conveniently be carried out at from −20° to +280° C.

Using the process according to the invention one can obtain monomeric condensation products as well as high molecular weight products which are both 2,4,5-triketoimidazolidines and polyamides, polyimides or polyamidoimides. Products having these groups possess particularly good processing characteristics.

It is not essential to mix all of the reaction components together; for example the reaction can be performed by initially introducing one component which may if desired be mixed with a small proportion of the second and/or third component and then the main quantity of the second and/or third reaction component may be added. This can be performed either in solution or in the melt. A catalyst can be added to the initial reaction component and/or the subsequently added reaction components. It is also possible to react only two components together and then to react the third in a further reaction stage; for example the polybasic carboxylic acids can be reacted, at least partly, with the isocyanate e.g. with the formation of imides or amides whilst in a second stage reaction takes place with the oxamidate and, if desired, in a further stage reaction with the remaining carboxylic acid is effected. This reaction in two stages is illustrated in equations (4) and (5). As the product still contains two reactive end-groups these can generally react with other isocyanate groups and, if desired, with oxamidate groups so as to result in chain elongation, e.g. with amide or imide formation according to equation (6), and possible also with branching.

In equations (4) or (6):

R$_{tr}$ is a trivalent carbocyclic or heterocyclic aliphatic group, mono- or polynuclear cycloaliphatic, aliphatic-aromatic or aromatic hydrocarbon group with 2 to 20 carbon atoms which may be substituted by alkyl, halogen or amino groups.

R$^{IV}$ and R$^V$, which may be the same or different, may each be aliphatic hydrocarbon groups with up to 18 preferably up to 6 C-atoms, cycloaliphatic hydrocarbon groups with up to 8 C-atoms, mononuclear aromatic hydrocarbon groups with 6 C-atoms which may be substituted by a hydrocarbon group having up to 14 C-atoms.

In compound VI the newly formed imide bond is shown after reacting the anhydride groups of compound V with the isocyanate II. The free isocyanate group can react further according to equation (5) with oxamidates to form triketoimidazolidine rings; the free ester group of compound V can react with further isocyanate e.g. with compound II, III, or VI with chain elongation and formation of further triketoimidazolidine rings. The reactions according to equations (4) to (6) are accompanied by the elimination of alcohol or carbon dioxide. Since these are condensation reactions they are not necessarily limited to the usual tricarboxylic acids so that di- and other polycarboxylic acids can be used. The carbon dioxide or alcohol evolved can be used as blowing agent if one is seeking to prepare foamed products. It is of course, also possible to produce foamed products using conventional blowing agents such as paraffin hydrocarbons with 5 to 9 C-atoms. It is also possible to react the oxamidate with the isocyanate in a first stage e.g. so as to form compounds of formula IX wherein Q and Q' represent one of —NH—CO—OR$^{IV}$, —NH—CO—COOR$^v$, R or R''', R$^{IV}$ and R$^v$ have the above meanings and in a second stage to react compound (IX) with the polycarboxylic acid.

In the products obtained according to the invention the terminal groups may be the same as those present in compounds I or IV. It is also however possible for both terminal groups to be oxamidate or for these ester groups to be at one end whilst a urethane or isocyanate group is at the other end or for both terminal groups to be urethane or isocyanate. In the preparation of branched products the terminal groups can vary still further.

Depending on the reaction conditions with the process according to the invention it is possible to obtain monomeric or polymeric compounds. It is also possible to obtain branched monomers or polymers when starting e.g. with at least trivalent isocyanates, at least trivalent carboxylic acids or at least trivalent oxamidates or a mixture of these polyvalent components mixed, if desired, with mono- or divalent components. If branching is to occur at the tricarboxylic acid radical the free acid should be reacted with three mols of isocyanate so that amide connection takes place in three directions in a manner analogous to that depicted in equation (4). The three isocyanate groups may then be reacted e.g., with two or three moles of oxamidate with the formation of two or three trikoimidazolidine groups.

Monomer compounds can be prepared in this manner with three or more triketoimidazolidine groups. For example this may be the case when starting with mono-oxamidates and tri-iso-cyanates. However in the preparation of these compounds it should be ensured that amino groups are not arranged in an o-position in the cyclic group R of the oxamidate or R$_{poly}$ of the polycarboxylic acids in order to avoid undesirable secondary reactions. Further possible products of this reaction are compounds (XXIX) and (XXX) as shown in the drawings. Thus polymeric compounds can also be prepared.

In formulae (XXIX) and (XXX)

R has the above meaning

R' has the meaning given hereinbefore for R'''

R'' has the meaning given for R and R and R'' can be the same or different

R''' has the above meaning for R' and R''' can be the same or different and R''' is at most tetravalent.

R$_{poly}$ is a di to hexavalent preferably, trivalent, carbocyclic or heterocyclic mono or polynuclear or an aliphatic group, e.g, a cycloaliphatic, aliphatic-aromatic or aromatic hydrocarbon group with 2 to 20 C-atoms which may be substituted by alkyl, halogen or amino groups and wherein the aliphatic group R$_{poly}$ may be saturated or it has one or more, especially two, olefinic double bonds, x is 0 or, if y = 1 y is 0 or an integer from 1 to 70 z is an integer from 1 to 6, preferably 1 to 3, and is at least 2 when Q is absent.

i and k which can be the same or different may be —NH—CO— or

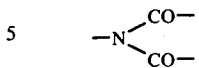

g and h are 1 or 2 provided the sum of $g+h$ is at most 3 $d,e,f$ and $j$ are 1 or 0 provided the sum of $d+e+f+j$ is at least 1 and provided one of the groups R and R''' is aromatic and further provided if R''' is aliphatic or cycloaliphatic the group R,R' or R'' adjacent to R''' is aliphatic.

As shown in formula (XXIX) R$_{poly}$ is only a di- or trivalent group. It is however possible to use a tetra, penta or hexavalent carboxylic acid. In such cases R$_{poly}$ is a tetra, penta or hexavalent radical and g and h are each an integer from 1 to 5 provided that $g+h$ is not more than 6. Extensive branching can occur at R$_{poly}$ as shown in formulae (XXXI).

If R$_{poly}$ is a carboxylic radical it generally has 6 to 34 carbon atoms, if it is an aliphatic hydrocarbon radical it may have 2 to 12 or 4 to 69 carbon atoms, respectively.

It is also possible for the branching point to be the group R'. In the compound of formula (XXIX) R, R', R'' and R'' can be branching points if they are polyfunctional. A further product obtained according to the invention in which branching takes place at the R' group is shown in formula (XXX) wherein the square brackets have the same meaning as in formula (XXIX). The molar ratios of the reaction components oxamidate, isocyanate and polycarboxylic acid can vary within wide limits. It can best be expressed by the following equation $$a(A') + c(C') = b(B')$$

wherein a is the number of oxadimate groups in $A'$ mols of oxamidate b is the number of isocyanate groups in $B'$ mols of isocyanate and c is the number of carboxy groups in $C'$ mols of polycarboxylic acid provided that a and b are always integers from 2 to 4 and c is an integer from 2 to 6. $A'$ is 0.97 to 0.03 mol. $C'$ is 0.03 to 0.97 mol, provided the sum of $A'$ and $C'$ is always 1. $(b,B')$ can be up to 3 times preferably up to 1.1 times larger than $(a.A' + c.C')$.

Oxamidates, isocyanates and polycar oxylic acids can all be employed as a single components or as mixtures of their type.

In the reaction between oxamidates, isocyanates and polycarboxylic acids with the above-indicated molar ratios, depending on the reaction conditions, products with only a moderately high degree of polymerisation can be obtained. For example, 1 mol of bisoxamide can react with 1 mol of di-isocyanate and then with 1 mol of a di- or tricarboxylic acid anhydride or the free acid so that only 1 isocyanate group is available for cylisation and the other acts as condensation agent and mops up alcohol liberated during the cyclisation by forming a urethane group. This urethane group (which can be called a pseudoisocyanate) may now be reacted at elevated temperature, with or without the catalyst, with the carboxy group of the polycarboxylic acid to form an amide or imide compound with the evolution of alcohol and carbon dioxide. This reaction proceeds according to equation (8) (see also equations (2) and (9)) with the formation of compound (XXXIII). Polymers of compound (XXXIII) can also be obtained in which case $f$ is more than 1. In these cases alcohol liberated during the cyclisation processes can be bound either intramolecularly in the polymer and/or extramolecularly to the unreacted isocyanate. The products may thus contain the terminal groups

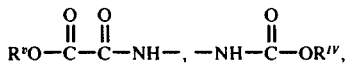

$R^{IV}$ and $R^V$ can then be different if a mixture of oxamidates with varying alkyl groups are used.

As can be seen the new process allows the reaction of completely different starting materials which can in addition be monomeric, polymeric, straight-chained or branched.

A furtheradvantage of the process of the invention is that whereas in previously proposed processes the reaction of polycarboxylic acid of their anhydrides with polyisocyanates at temperatures above 80° C often lead to insoluble imide group-containing polymers the processing of which is very difficult, the reaction of the same components with concomitant use of an oxamidate in the above indicated mixing ratios provides clear readily processable polymer solutions.

The process according to the invention can be performed over a wide temperature range. Thus the reaction can be performed in the absence or advantageously in the presence of solvents at temperatures of $-20°$ to $+280°$ C preferably at 0° C to 180° C. The reaction is exothermic and proceeds in many cases at room temperature or at slightly elevated temperature e.g. at 40° to 50° C. It may be advantageous to heat the reaction components to drive the reaction to completion when using less reactive components such as isocyanates or polycarboxylic acids or their anhydrides. It is also possible to react the starting products in the melt and, if desired subsequently in a solvent preferably a phenolic solvent.

The reaction can take place in those solvents in which the reaction products are insoluble e.g. in ligroin, benzene, toluene, chlorobenzene, nitrobenzene, cyclohexane, xylene, ethylacetate or butylacetate. Alternatively the reaction may be effected in solvents in which the products are soluble such as N,N'-dimethylformamide, N,N'-dimethylacetamide, dimethylsulphoxide, N-methyl-pyrrolidone, N,N',N''-hexamethylphosphoric acid triamide, phosphoric acid-tris-(dimethylamide), cyclohexanone, isophorone, acetophenone and phenols with up to 10 C-atoms e.g. phenol, cresol and xylenol. In addition to the above solvents the products are also soluble in ketones such as acetone, methylethylketone and dibutylketone.

The solution of polycondensation products obtained can be used as such. By addition of a suitable precipitation agent such as water, alcohols, aliphatic and/or aromatic hydrocarbons the reaction products may be precipitated and separated from the solution as more or less coloured powders. The latter can also be obtained by evaporating these solutions in suitable apparatuses e.g. in spray dryers.

The process is also well suited to the preparation of symmetrical and unsymmetrical triketoimidazolidine compounds. This is for example possible by using a polycarboxylic acid of formula (XXVII) of the drawings.

If monomeric products are desired at least one monofunctional reaction component should be used as starting material e.g. a monoisocyanate or a monooxamidate.

Polymers can be prepared according to equation (7) if the pre-condensate contains polymerisable groups e.g. $-NH-COOR^{IV}$, $-NH-CO-COOR^V$ (hereinafter called Q and Q'), $-COOH$, $-COOR^V$, $-COOR^{IV}$, and $-N=C=C=O$, wherein $R^{IV}$ and $R^V$ have the meanings given above and may be the same or different. In equation (7) $n$ is an integer from 1 to 70 preferably 1 to 50. Polymer formation may be achieved if the monomeric reaction products obtained according to the invention either in solution or in solvent-free form in molten or solid state are heated to 120° to 550° C preferably to at least 200, and in particular to 280° to 450° C. Chemical-resistant, temperature-resistant, substantially insoluble film-forming polymers are formed. If a sufficiently high reaction temperature is selected e.g. 150° to 300° C the reaction of the terminal groups Q and Q' takes place at a satisfactory rate. Polymerisation is intended to mean the chain elongation by addition and/or condensation. The polymers can be separated by precipitation and filtration as pale yellow to brownish powders which are surprisingly soluble. They may be separated from such a solution substantially unchanged by adding water or alcohol. The compounds are thus obtained as powders or crystalline substances e.g. as micro-crystalline substances.

The degree of polymerisation of the products obtained may be adjusted by suitably selecting the reaction conditions (cf formula (XI) wherein $n$ is an integer from 1 to 70). Generally products without a particularly high molecular weight are obtained so that contrary to expectations the products have relatively good solubility in conventional aprotic solvents (e.g. dimethylformamide, N-methylpyrrolidone, dimethylsulphoxide, N,N',N''-hexamethylphosphoric acid triamide). Solutions of 30 to 70% concentration can be obtained without difficulties without the viscosity being unmanageable in such aprotic solvents. Even on storage the solutions remain unchanged and do not tend to crystallise. These properties mean the material possesses good processability and a variety of the products may be used to obtain polymeric heterocyclic compounds. Owing to the high molecular weight the products show good film-forming properties and high thermal stability. After hardening in most solvents insoluble polymers are obtained which can, under certain conditions, be prepared directly in one stage according to the invention. This can be of advantage in the production of chemically resistant moulded articles.

The thermal stability is particularly high in products having a low hydrogen content particularly when no aliphatic or cycloaliphatic-bonded hydrogen is present in a hetero ring system. Films and foils obtained from the preliminary products also possess very good elasticity properties. They have good adhesive power to metal surfaces.

The reaction according to the invention can take place with or without catalysts. Suitable catalysts are those which are used in reactions of isocyanates with compounds containing reactive hydrogen atoms such as tertiary bases e.g. amines viz. triethylamine, tributylamine, N-isobutylmorpholine, pyridine, N-methylpiperidine, N,N-dimethylaniline, or triethylenediamine; triphenylphosphine, trimorpholinophosphine or mixtures thereof. Other suitable catalysts are lithium methylate; lithium benzoate; sodium athylate; potassium tert.butylate; organo tin compounds such as dibutyl tin oxide, dimethyl tin stearate, dibutyl tin glycolate, dibutyl tin dilaurate, diphenyl tin oxide, ferrocene (dicyclopentadienyl-iron-(II)); metal chelates such as iron acetyl acetonate and cobalt complexes either alone or in combinations of such compounds.

Suitable oxamidates are those of formula (VII) of the drawings wherein R and $R^V$ have the above meaninigs and r is an integer from 1 to 6. Suitable isocyanates are those of formula (VIII) wherein R''' has the above meanings and s is an integer from 1 to 4.

The group R in the oxamidates may be a carbocyclic or heterocyclic group preferably having an aromatic character e.g. phenyl, napthyl, benzene, azophenyl, benzothiazolylphenyl, anthraquinonyl or pyrridyl.

Suitable bifunctional R radicals of the bisoxamidates are those of formulae (XII) to (XV) of the drawings wherein X = $-CH_2-$, $-O-$, $-S-$, $-S-S-$, $-SO_2-$, $-N=N-$, $-NR^{VII}-$, ($R^{VII}$ is an aliphatic, cycloaliphatic or aromatic group with up to 8 C-atoms) diphenylene, dimethyldiphenylene, anthraquninoylene, pyrridylene, quinonylene, thiophenylene, benzofurylene and N-methylcarbazolylene groups. The R group can be substituted in one or more aromatic and/or heterocyclic nuclei or in a side chain by one or more substituents that do not react with isocyanates under the conditions of the reaction. These substituents can be alkyl, alkoxy, halogenalkyl, ester, alkylketo, ($\omega$-m)-ketoalkyl or alkylsulphonyl groups with up to 5 carbon atoms wherein m is 1, 2 or 3. Examples of such substituents are $-CH_3$, $-C_2H_5$, $-OCH_3$, $-OC_2H_5$, $-CF_3$, $-COOC_2H_5$, $-CN$, $-COCH_3$ or $-SO_2CH_3$. Other possible substituents are nitro, cyano or halogen in particular F, Cl or Br. Similarly it is possible also to use tris and/or tetrakisoxamidates either alone or mixed with the bisoxamidates. An oxamidate containing the group of formula (XIII) is the compound (XXXII).

If R is an aromatic or heteromatic radical it generally has 6 to 20 carbon atoms, if it is substituted the substituents thereof have up to 18 carbon atoms.

The group R''' in the isocyanate may be a mono to tetravalent group c.g. an aliphatic, cycloaliphatic, aromatic or mixed aromatic-aliphatic group with generally up to 20, preferably up to 15 carbon atoms e.g. cyclohexyl, butyl, octyl, octadecyl, ethylene, propylene, butylene as well as the groups of formulae (XII) and (XIII) wherein X is $-CH_2-$ or $-O-$ and formulae (XVI) to (XIX) of the drawings.

These groups can be substituted by at least one alkyl, alkoxy or halogeno alkyl group with, in each case up to 5 carbon atoms, nitro groups or halogen in particular F, Cl or Br. Examples of such substituents are $-CH_3$, $-C_2H_5$, $-OCH_3$, $-OC_2H_5$ or $-CF_3$. Several aromatic rings can be connected by $-CH_2-$, $-O-$, $-S-$, $-S-S-$, $-SO_2-$, $-CO-$ or $-N=N-$. Advantageously in each R''' group more than 5 H-atoms are substituted by such groups.

If R''' is a carboxylic radical it generally has 6 to 30 carbon atoms. It it is a heterocyclic radical it generally has 6 to 40 carbon atoms. If these two types of radicals are substituted the substituents have at most 18 carbon atoms.

$R^{IV}$ and $R^V$ in the oxamidates may be alkyl group with up to 6 carbon atoms preferably $-CH_3$, $-C_2H_5$ or $-C_4H_9$, phenyl or phenyl substituted by alkyl such as methyl, ethyl or butyl.

Suitable isocyanates are 3,3'-dimethyl-diphenylmethane4,4'-diisocyanate; tri- and tetravalent isocyanates, e.g. 2,4,6-triisocyanato-toluene; 4,4',4''-triisocyanato-triphenylmethane; 2,4,4'-triisocyanato-diphenylmethane; 2,2',5,5'-tetraisocyanato-diphenylmethane; trivalent isocyanates of formula (XX) obtained by the addition of trimethylolpropane to tolylenediisocyanate; an isocyanate of formula (XX) obtained by reacting hexamethylenediisocyanate and water; or isocyanates with up to four free isocyanate groups of formula (XXII) as are obtained by reacting tolylene-diisocyanate and hexamethylenediisocyanate.

The tri- and tetraisocyanates can be substituted by the same substituents as the di-isocyanates.

Isocyanate forming components may be used in place of the free isocyanates for example one may be a urethane such as diphenylmethane-4,4'-bis-(phenylcarbaminate), diphenylethane4,4'-bis-(butylcarbaminate) or a disubstituted carbamic acid such as diphenyl-4,4'-bis-(diethylamidecarbaminate).

Suitable polybasic carboxylic acid components are the following carboxylic acids or their anhydrides: isophthalic, bromoisophthalic, 5-aminoisophthalic, trimellitic, pyromellitic, terephthalic, 2,5-dianilino-terephthalic, 2,5-ditoluidino-terephthalic, 4-aminonaphthalic, 4,4-methylenebis-anthranilic, hemimellitic, mellitic, maleic, fumaric, itaconic, muconic, hexahydroterephthalic, adipic, glutaric, succinic sebacic, suberic, 1,12-dodecane dicarboxylic, tetrahydrofurantetracarboxylic, benzophenonetetracarboxylic, 1,4,5,8-naphthalenetetracarboxylic, and perylenetetracarboxylic acid, pyrazenetetracarboxylic (cf. formula XXVIII) and benzophenonehexacarboxylic acid dilactone and derivatives thereof e.g. substituted by halogen, such as chlorine, bromine and/or alkyl groups with 1 to 8 carbon atoms. There may also be used condensed systems having at least 2 carboxyl groups in the molecule such as e.g. N,N'-terephthaloyl-bisglycinc, N,N'-isophthaloyl-bisglycine, bis carboxymethylamino-diphenylmethane (or diphenyl ether or diphenyl sulphone). Other suitable materials for the reaction are the carboxylic acids of formula (XXIV) to (XXVIIIa), (XXXIV), XXXVIII, and (XXXV). The compound shown in Formula XXXIV may be a di-, trior a tetracarbocyclic acid. The anthraquinonylene group in compound (XXXV) can be substituted in the 1,5 or 1,8 positions. Still further suitable carboxylic acids are those acids substituted by amino groups e.g. the product obtained by reacting maleic or mellitic anhydride with diaminodiphenylmethane, diaminodiphenylether, diaminodiphenylsulphone; p-phenylenediamine or m-phenylenediamine with amide formation and the liberation of a carboxyl group of maleic or mellitic anhydride.

Using the process according to the invention it is possible to obtain yields of N,N'-disubstituted 2,4,5-triketoimidazolidines that are 90% or more of theory.

It is possible to increase the molecular weight of monomeric or higher molecular weight, e.g. oligomeric, reaction products prepared according to the invention by heat treatment at temperatures of from 200°to 550° C preferably from 260°to 480° C so as to obtain a material possessing particularly good thermal stability and which is almost insoluble in conventional solvents.

The monomeric and polymeric and in particular the low molecular weight compounds prepared according to the invention have a wide range of uses e.g. they are valuable intermediates for organic syntheses. As a low molecular material they are useful starting materials for the preparation of pharmaceuticals; pesticides such as insecticides, myocides and bactericides; and also for the synthesis of dyes and plastics and for the stabilisation of high molecular weight materials such as polymerisation and condensation resins.

The products and polymers produced by the process of the invention are particularly suited for coating metallic moulded articles such as wires, sheets, plates, pipes and preferably electric conductors where it is unimportant whether the application takes place in powder form or in solution. In the same way they can be applied to ceramic moulded articles. After thermal polycondensation a coating is obtained on these objects that possesses good adherence, high temperatureresistance and good thermal stability. In powder form the products are particularly suited for the production of moulded articles by a hot moulding process when admixed with an inorganic filler such as mineral powders, glass flour, glass fibers, asbestos fibres, graphite, metal powders and chippings. The formation of the moulded articles may be effected at elevated temperatures e.g. 280°–500° C and at high pressures e.g. 50–5000 atm. Additionally transparent, oven glass-clear foils, films and fibres can be formed therefrom. By the addition of blowing agents (although, as mentioned above, blowing agents may be unneccessary as alcohol and carbon dioxide are liberated) foamed products can be obtained possessing high temperatures resistance; such foams being particularly useful for insulation purposes. A further use for the products is as stabilisers for poylmeric products in particular for polymerisation and/or polycondensation resins. They can also however be mixed with such polymers including the polymerization and/or condensation resins containing heterocyclic groups at temperatures of from −10° to +250° C. preferably +20° to +190° C in solution, the melt or in solid phase and be further procesed to moulded articles and/or coatings.

In order that the invention may be well understood the following Examples are given by way of illustration only.

EXAMPLE 1

605g (2.4 mols) of 4,4'-diisocyanato-diphenylether are dissolved in 924g of an N-methylpyrrolidone: cyclohexanone mixture (30:70% by weight) at 100° C. After adding 16g of triethylamine over a period of 1 hour 318.5g (0.8 mol) of 4,4'-bis(ethoxalylamino)diphenylmethane (formula (XXXII)) are introduced. The temperature of the mixture is maintained by cooling at from 105° to 110° C and towards the end of the addition the viscosity rises. The mixture is stirred for 4 hours at 105°–110° C. Thereafter a solution of 76.8g (0.4 mol) of trimellitic anhydride in 240g of N-methyl-pyrrolidone is added dropwise over a period of 1 hour at 105° C. The viscosity of the clear reaction product rises further. Subsequently stirring takes place at 100° C until the evolution of $CO_2$ has ended which occurs after approximately 2–4 hours.

2154g of a clear red-brown highly viscous polymeric solution (solids content 46% by weight) are obtained. An iron plate coated with this solution was stoved at 350° C and a transparent orange-yellow coating was obtained.

EXAMPLE 2

199g of 4,4'-bis(ethoxalylamino)-diphenylmethane (0.5 mol) and 96g (0.5 mol) of trimellitic anhydride are heated to 120° C with 544g of N-methylpyrrolidone after adding 1g of lithium benzoate and 5ml of tri-nbutylamine 250g (1 mol) of 4,4'-diisocyanatodiphenylmethane are then introduced over a period of 30 minutes. Subsequently the mixture is stirred at 120 ° C for 4–6 hours until the evolution of $CO_2$ has ended. After cooling 1065g of a clear highly viscous polymer solution are obtained.

EXAMPLE 3

199g (0.5 mol) of 4,4'-bis-(ethoxalylamino)-diphenyl methane 96g (0.5 mol) of trimellitic anhydride, 1g of lithium benzoate and 5g of triethylamine ar dissolved in 670g of N-methyl pyrrolidone:dimethylformamide (weight ratio 1:1). After heating the mixture to 150° C 375g (1.5 mol) of 4,4'-diisocyanato diphenylmethane are introduced over a period of 120 minutes. After cooling to 110° C the reaction mixture is stirred for 4 hours to terminate the condensation. On cooling 1185g of a viscous clear red-brown polymer solution are obtained.

EXAMPLE 4

756g (3 mol) of 4,4'-diisocyanato diphenylether are heated to 110° C in 1154g of N-methylpyrrolidone: cyclohexanone mixture (weight ratio 30:70) and after adding 20 ml of triethylamine 398g (1 mol) of 4,4'-bis-(ethoxalylamino)-diphenylmethane are added over a period of 2 hours. After 45 minutes 161g (0.5 mol) of benzophenonetetracarboxylic acid dianhydride are added over one hour with vigorous stirring. The viscosity rises sharply and, after three hours at 100°–110° C a clear red-brown polymer solution is obtained. Yield 2,400g (solids content approximately 52%).

EXAMPLE 5

398g (1 mol) of 4,4'-bis-(ethoxalylamino)-diphenyl methane and 96g (0.5 mol) of trimellitic anhydride are dissolved in 1,000g of N,N'-dimethylformamide: cyclohexanone (weight ratio 40:60) at 40° C. After adding 15 ml of triethylamine and 1g of ethylhexyltitanate 522g of 2,4-tolylene diisocyanate are added dropwise in such a way that the temperature does not exceed 50° C. The mixture is stirred for two hours at 50° C and 1890g of a clear viscous solution with a 50% solids content are obtained.

EXAMPLE 6

134g (0.5 mol) of naphthalenetetracarboxylic acid dianhydride and 398g (1 mol) of 4,4'-bis-(ethoxalylamino)-diphenylmethane are dissolved at 100° C in 1150g of a mixture of N-methylpyrrolidone:dimethylsulphoxide (weight ratio 45:55) and over a period of 3 hours 756 g of 4,4'-diisocyanato diphenylether (3 mol) are added with vigorous stirring under an inert gas atmosphere. The mixture is then stirred for 2 hours at 100° C and 2390g of a dark brown viscous polymer solution are obtained. The viscosity of this solution is above 100,000cP at 20° C.

Working in an analogous manner but reacting 731g (2.9 mol) instead of 756g of the 4,4'-diisocyanato diphenylether together with 15.4g (0.1 mol) of mchlorophenylisocyanate a polymer solution is obtained with a viscosity of only 30,000cP at 20° C.

EXAMPLE 7

398g (1 mol) of 4,4'-bis-(ethoxalylamino)-diphenyl methane and 188g (0.5 mol) of 2,5-bis-(toluidino)-terephthalic acid are dissolved in 1336g of dimethyl sulphoxide:N,N'-dimethylacetamide (weight ratio 1:1) and heated to 100° C with 5g of diazabicyclo-2,2,2-octane as a catalyst. Subsequently at 100°–120° C 750g (3 mol) of 4,4'-diisocyanato diphenylmethane are introduced. The viscosity increased greatly and the reaction mixture becomes dark brown-red. The mixture is stirred for 2 hours at 100°–120° C and 2630g of a clear highly viscous polymer solution are obtained.

Example 8

398g (1 mol) of 4,4'-bis-(ethoxalylamino)-diphenylmethane and 106.5g (0.5 mol) of 4-aminonaphthoic acid anhydride are dissolved in 1026g of N-methylpyrrolidone and after adding 20ml of triethylamine heated to 130° C. 522g (3 mol) of 2,4-tolylene diisocyanate are then added dropwise over 1 hour. The mixture is stirred for 2 hours at 100° C and 2035g of a clear brown polymer solution are obtained.

EXAMPLE 9

161g (0.5 mol) of benzophenonetetracarboxylic acid dianhydride and 398g (1 mol) of 4,4'-bis-(ethoxalyl amino)-diphenylmethane are dissolved in 1018g of N-methyl pyrrolidone at 100° C and 10ml of tribenzylamine are added. Over a period of three hours 255g (3 mol) of 2,4-tolylene diisocyanate are added dropwise at 120°–140° C. The reaction mixture is stirred for 2 hours at 100° C and 2,100g of a high viscous orange red polymer solution are obtained.

EXAMPLE 10

199g (0.5 mol) of 4,4'-bis-(ethoxalylamino) diphenylmethane and 250g (1 mol) of 4,4'-diisocyanato diphenylmethane are dissolved at 100° C in 511g of N-methylpyrrolidone:cyclohexanone (weight ratio 30:70). After adding 10ml of triethylamine the reaction mixture is heated to 135° C. The mixture is maintained at 100° C for 2 hours over which period the viscosity of the solution rises sharply. Thereafter 62g (0.25 mol) of tetrahydrofurantetracarboxylic acid dissolved in 186g of N-methylpyrrolidone are added dropwise over 10 minutes. Stirring is continued at 100° C until the evolution of $CO_2$ is over and 1190g of a clear polymer solution are obtained.

EXAMPLE 11

796g (2 mol) of 4,4'-bis-(ethoxalylamino)diphenylmethane and 756g (3 mol) of 4,4'-diisocyanato diphenylether are dissolved in 1,000ml N-methylpyrrolidone and heated to 80° C. The reaction is exothermic and the temperature rises to 143° C. After the reaction has subsided at 130° C, 140g (0.5 mol) of N,N-terephthaloylbis-glycine dissolved in 692g of N-methylpyrrolidone are added over 1 hour. The reaction mixture is stirred for 4 hours at C and 3340g of product are obtained.

EXAMPLE 12

796g (2 mol) of 4,4'-bis-(ethoxalylamino)diphenylmethane and 140g (0.5 mol) of N,N'-terephthaloyl bis-glycine are dissolved at 100° C in 1,000ml of N-methylpyrrolidone after adding 20ml of thiethylamine. After stirring for 1 at 100° C a solution of 756g (3 mol) of 4,4'-diisocyanato diphenylether in 692g of N-methylpyrrolidone are added over 30 minutes. The temperature rises to 106°–108° C. The mixture is stirred for a further 4 hours at 100° C and 3335g of a clear red-brown viscous solution having a greenish fluorensence are obtained.

EXAMPLE 13

272g (0.5 mol) of 4,4'-bis-(4-carboxyphthalimido)-diphenylmethane and 199g (0.5 mol) of 4,4'-bis-ethoxalylamino)-diphenylmethane are heated in 1040 g of N-methylpyrrolidone to 120° C with 5ml of added tributylamine. 375g (1.5 mol) of 4,4'-diisocyanato diphenylmethane are added over 90 minutes. Fine crystals separate from what was a clear solution. Condensation is effected at 190° –198° C until the reaction mixture which is transparent and viscous at room temperature gives a clear viscous polymer solution; this occurs after about 8–10 hours. 1790g of a clear highly viscous polymer solution were obtained.

EXAMPLE 14

213g (0.5 mol) of 4,4'-bis-(ethoxalylamino)3,3'-dimethyl diphenylmethane (melting point 136° C) and 250g (1 mol) of 4,4'-diisocyanato diphenylmethane are dissolved in 800g of dimethylformamide at 80° C. After adding 1.0g of n-butyltitanate and 5ml of tributylamine the temperature rises to 92°–95° C owing to the exothermic reaction. After stirring for 2 hours the temperature rises to 160° C and 57.6g (0.3 mol) of trimellitic anhydride are introduced over 30 minutes. The mixture is stirred at 160° C for 6 hours and after cooling 1290g of a clear viscous polymer solution are obtained.

EXAMPLE 15

98.4g (0.2 mol) of crude 1,4-bis-(p-ethoxalylamino) diphenyl ether (melting point 165° C) and 19.2g (0.1 mol) of trimellitic anhydride are dissolved in 100ml of dimethylacetamide at 130° C and mixed with 0.5 ml of tribenzylamine. OVer a period of one hour and at this temperature a mixture of 47.5g (0.15 mol) of 4,4'-diisocyanatodiphenylmethane and 45.4g (0.18 mol) of 4,4'-diisocyanato diphenylether are introduced. The mixture is stirred for 4 hours at 140° C and cooled to 70° C and then 100g of technical cresol is stirred in. After cooling to room temperature 402g of a clear highly viscous polymer solution with a solids content of about 50% are obtained.

EXAMPLE 16

A mixture of 199g (0.5mol) of 4,4'-bis (ethoxalylamino)diphenylmethane (melting point 148° C), 200g (0.5 mol) of 4,4'-bis-(ethoxalylamino) diphenyl ether (melting point 140° C) and 10.9g. pyrromellitic acid dianhydride (0.05 mol) are dissolved at 70° C in 750g of a dimethylsulphoxide: N-methylpyrrolidone mixture (weight ratio 70:30). After adding 5g of triethylamine and 0.05g of lithium benzoate, 325g (1.3 mol) of 4,4'-diisocyanatodiphenylether are added over 2 hours. The temperature rises to about 90° C and after stirring for about 3 hours at 80°–90° C the mixture is cooled to room temperature. 1465g of a clear red-brown highly viscous polymer solution are obtained with a solids content of about 49%.

EXAMPLE 17

1,000g of polymer solution prepared according to Example 16 are added dropwise over 2 hours with vigorous stirring to 3,000ml of ethyl alcohol at 60°C. A light yellow polymer separates and is suction filtered, and after precipitation washed with 1,000ml of an ethanol:toluene mixture (weight ratio 1:1) and dried in vacuo at 100° C. 475g of a free flowing, slightly yellowish polymer powder are obtained with a softening range of 140°-150° C.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

We claim:

1. A polymer reaction product containing a plurality of units of the formula

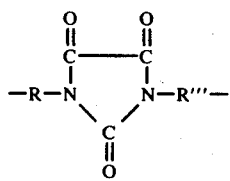   (I)

together with more than one unit selected from the group consisting of

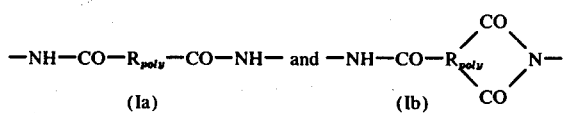 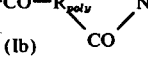

(Ia)    (Ib)

and

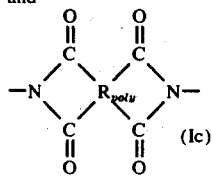   (Ic)

and obtained by reaction at a temperature in the range of −20° to 30 280° C at least one oxamidic ester (a) of Formula VII, $$R-(NH-CO-CO-OR'')_r \quad (VII)$$

at least one isocyanate (b) of Formula VIII $$R'''-(N=C=O)_s \quad (VIII)$$

or compound forming an isocyanate under the aforesaid reaction conditions and at least one polycarboxylic acid or polycarboxylic acid anhydride forming a polycarboxylic acid under the aforesaid reaction conditions (c) of the formula $R_{poly}(COOH)_p$ in which formulae R is a member selected from the group consisting of aa. an at least mono-nuclear di- to hexavalent aromatic radical having 6 to 18 carbon atoms,
bb. an at least mono-nuclear di- to hexavalent heterocyclic radical having 5 to 12 carbon atoms,
cc. a radical as defined in (aa) being substituted by at most two substituents, referred to any one aryl group of the radical selected from the group consisting halogen, nitro, dialkylamino, diarylamino, alkylaryl-amino groups, alkyl, alkoxy, carboxyalkyl, carboxyaryl, acyl, cycloalkyl, halogenated alkyl, halogenated alkoxy, halogenated carboxyalkyl, halogenated carboxyaryl and halogenated acyl groups with up to 18 carbon atoms,
dd. a radical as defined in (bb) being substituted by a substituent selected from the group consisting of halogen, nitro, dialkylamino, diarylamino, alkylarylamino groups, alkyl, alkoxy, carboxyalkyl, carboxyaryl, acyl, cycloalkyl, halogenated alkyl, halogenated alkoxy, halogenated carboxyalkyl, halogenated carboxyaryl or halogenated acyl groups with up to 18 carbon atoms,
ee. a quinonyl radical;

$R^V$ is an aliphatic hydrocarbon group having up to 18 carbon atoms, a cycloaliphatic hydrocarbon group with up to 8 carbon atoms, an unsubstituted mononuclear aromatic hydrocarbon group or a mononuclear aromatic hydrocarbon having one or more hydrocarbon substituents, said substituents having a total of up to 14 carbon atoms, $R'''$ is a member selected from the group consisting of d1. an at least mono-cyclic di- to tetravalent carboxylic radical having 6 to 30 carbon atoms,
e1. an at least mono-cyclic di- to tetravalent heterocyclic radical having 6 to 40 carbon atoms,
f1. a radical d1) being substituted by at least one of the groups halogen, nitro, alkyl, alkoxy, carboxyalkyl, carboxyaryl, acyl, cycloalkyl, halogenated alkyl, halogenated alkoxy, halogenated carboxyalkyl, halogenated carboxyaryl and a halogenated acyl with up to 18 carbon atoms,
g1. a radical as defined in (e1) being substituted by at least one of the groups halogen, nitro, alkyl, alkoxy, carboxyalkyl, carboxaryl, acyl, cycloalkyl, halogenated alkyl, halogenated alkoxy, halogenated carboxyalkyl, halogenated carboxyaryl and halogenated acyl with up to 18 carbon atoms,
h1. an aliphatic radical with 1 to 20 carbon atoms;

$R_{poly}$ is a member selected from the group consisting of i1. an unsubstituted di- to hexavalent at least monocyclic radical having 6 to 34 carbon atoms,
k1. an at least mono-nuclear carboxylic radical having 6 to 34 carbon atoms being substituted by halogen, amino or alkyl groups having a total of 1 to 8 carbon atoms,
l1. an aliphatic di- to hexavalent hydrocarbon radical having 2 to 12 carbon atoms and which may have at least one double bond,
m1. a heterocyclic radical having 4 to 69 carbon atoms
o1. an aliphatic radical (l1) being substituted by alkyl, halogen or amino groups,
p1. a heterocyclic radical (m1) being substituted by alkyl, halogen or amino groups, $r$ is an integer from 2 to 6,
$s$ is an integer from 2 to 4 and
$p$ is an integer from 2 to 6, and in which polymer reaction products 1 to $r$ mols of oxamidic ester have been reacted with one mol of isocyanate or 1 to $s$ mols of isocyanate have been reacted with one mol of oxamidic ester with the provisions that I. more than $1/r$ of the alcohol groups of the oxamidic ester (a) have been removed by reaction with the isocyanate groups when an excess of ester groups of the oxamidic ester, referred to the isocyanate groups, have been used as starting material and that II. more than $1/s$ of the isocyanate groups of the isocyanate (b) has been reacted, when an excess of isocyanate groups, referred to the ester groups of the oxamidic ester, has been used as a starting material, and III. in which reaction product at least two ester groups of the oxamidic ester have been reacted, where an excess or equimolar amount of isocyanate has been used, and at least 2 isocyanate groups have been reacted where an excess or equimolar amount of ester groups of the oxamidic ester has been used, and IV. wherein components (a) and (c) have been reacted in a molar proportion of (A') (0.97 to 0.03) to (C') (0.03 to 0.97) wherein the total of both components is always one mol provided the oxamidic ester and the polycarboxylic acid have the same functionality and wherein the molar proportion of the reaction components is $$a(A') + c(C') = b(B')$$

wherein $a$ is the number of oxamidic ester groups in said $A'$ mols of oxamidic ester, $b$ is the number of isocyanate groups in said $B'$ mols of isocyanate, $c$ is the number of the carboxylic groups in $C'$ mols of polycarboxylic acid and $a$ and $b$ are integers of from 2 to 4 and $c$ is an integer from 2 to 6 and wherein $b(B')$ is up to three times the amount of $a(A') + c(C')$.

2. The polymer reaction product of claim 1 obtained by reacting the oxamidic ester (a), the isocyanate (b) and the polycarboxylic acid (c) wherein the polycarboxylic acid has 4 to 71 carbon atoms and two to six carboxylic groups.

3. A polymer reaction product of claim 1 which is the reaction product of
   a. a diphenyl compound with bis-(ethoxalylamino) substituents of Formula XIII

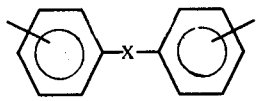

(XIII)

wherein X is —CH$_2$— or —O—,
   b. a diisocyanate of Formula VIII

R''—(N=C=O)$_s$ (VIII)

wherein $s$ is 2 and R''' is an aromatic or mixed aromaticaliphatic group of Formula XIII,

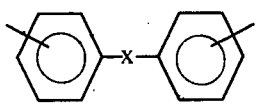

(XIII)

and wherein X is —CH$_2$— or —O—, and having up to 15 carbon atoms, and c. a dicarboxylic to tetracarboxylic acid having 4 to 71 carbon atoms or an anhydride thereof.

4. A polymer product of claim 3 which has been obtained by reacting the product of
   a. 4,4'-bis-(ethoxalylamino)-diphenylmethane,
   b. 4,4'-diisocyanato-diphenylmethane, and
   c. trimellitic acid anhydride.

5. A polymer product as claimed in claim 1 wherein in Formula VII

R—(NH—CO—CO—OR$_r$)$_r$ (VII)

R$^V$ is selected from the group consisting of alkyl with up to 18 carbon atoms, cycloalkyl with up to 8 carbon atoms, mononuclear aryl with 6 carbon atoms being unsubstituted or substituted by a hydrocarbon group having up to 14 carbon atoms; and wherein in Formula VII R'''—(N=C=O)$_s$ (VIII)

R''' is selected from the group consisting of a mono- and a binuclear aryl radical selected from the group consisting of Formulae XII to XIV

(XII)

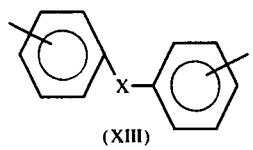

(XIII)

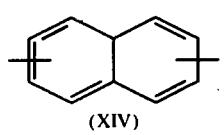

(XIV)

wherein X is —CH$_2$— or —O— which aryl radical being substituted with alkyl, halogen or unsubstituted and having 6 to 20 carbon atoms; aliphatic hydrocarbon group with 1 to 20 carbon atoms, and cycloaliphatic hydrocarbon group with 5 to 12 carbon atoms; and wherein $r$ and $s$ have meaning as defined in claim 1.

6. A polymer product of claim 1 produced by reacting:
   a. an oxamidic ester selected from the group consisting of 4,4'-bis(ethoxyalylamino)diphenylmethane, 4,4-bis (ethoxalylamino)diphenyl ether, and mixtures thereof,
   b. an isocyanate selected from the group consisting of 4,4'-diisocyanato-diphenylmethane, 4,4'-diisocyanatodiphenyl ether, 2,4-toluene-diisocyanate, and mixtures thereof,
   c. a polycarboxylic acid selected from the group consisting of trimellitic acid, pyromellitic acid, benzophenonetracarboxylic acid, naphthalenetetracarboxylic acid, 2,5-bis-(toluidino)tetraphthalic acid, 4-aminoaphthoic acid, tetrahydrofuran-tetracarboxylic acid, N,N-terephthalolyl-bis-glycine, 4,4'-bis(4-carboxy-phthalimido)diphenylmethane, and anhydrides thereof and mixtures thereof.

7. A polymer reaction product of claim 1 produced by reacting (a), (b), and (c) at a temperature in the range of 0° to 180° C.

8. A polymer product of claim 1 which is produced by reacting (a), (b), and (c) in the presence of a catalyst, containing at least one reactive hydrogen atom and selected from the group consisting of at least one amine, phosphine, an organic lithium or tin compound, ferrocene iron acetyl acetonate and cobalt complexes.

9. A polymer product of claim 8 wherein the catalyst is selected from the group consisting of lithium benzoate, diazabicyclo 2,2,2-octane, n-butyl titanate, triethylamine, tributylamine, ethylhexyltitanate, tribenzylamine, triphenylphosphine, trimorpholinophosphine and mixtures thereof.

10. A polymer product of claim 1 produced by reacting (a), (b), and (c) in the form of a solution or a dispersion in a solvent.

11. A polymer product of claim 1 containing at least one unit selected from the group consisting of:

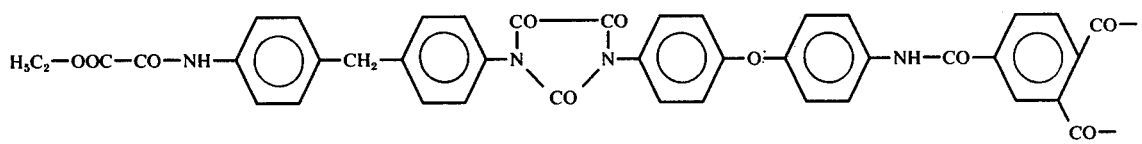

and mixtures thereof.

12. A polymer product of claim 1 containing at least one unit of the formula

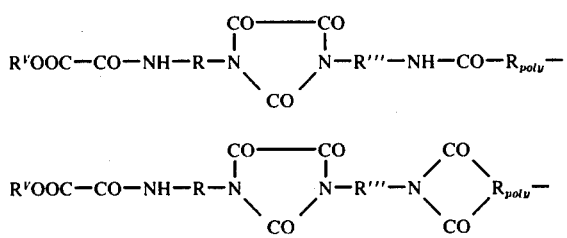

13. A polymer product of claim 1 obtained by reacting:
 I. an oxamidic ester selected from the group consisting of 4,4'-bisethoxalylaminodiphenylmethane, 4,4'-bisethoxalyl-aminodiphenyl ether, 1,4-bis-(p-ethoxalylaminophenoxy)benzene, and mixtures thereof;
 II. an isocyanate selected from the group consisting of 4,4'-diisocyanato-diphenylmethane, 4,4'-diisocyanatodiphenyl ether, 2,4-toluenediisocyanate, and mixtures thereof;
 III. a polycarboxylic acid selected from the group consisting of trimellitic acid, benzophenonetetracarboxylic acid, naphthalenetetracarboxylic acid, 2,5-bis-(toluidino)-tetraphthalic acid, 4-aminonaphthoic acid, tetrahydrofuran-tetracarboxylic acid, N,N-terephthalolyl-bis-glycine, 4,4'-bis-(4-carboxyphthalimido)diphenylmethane and anhydrides thereof and mixtures thereof;
 IV. a catalyst selected from the group consisting of lithium benzoate, diazabicyclo, 2,2,2-octane, n-butyl titanate, triethylamine, tributylamine, tribenzylamine, ethyhexyltitanate, triphenylphosphine, trimorpholinophosphine and mixtures thereof;
 at a temperature in the range of 0° to 198° C;
 wherein the molar ratios of reaction components (I), (II), and (III) are given by the equation:
 $a(A') + b(B') = c(C')$ wherein $a$ is the number of oxamidic groups in $A'$ mols of the oxamidic ester; $b$ is the number of isocyanate groups in $B'$mols of the isocyanate; $c$ is the number of carboxy groups ind $C'$mols of the polycarboxylic acid;
 wherein $a$ and $b$ are integers from 2 to 4 and $c$ is an integer from 2 to 6;
 wherein $A'$ is in the range of 0.97 to 0.03; $C'$ is in the range of 0.0.3 to 0.97;
 wherein the sum of $A'$ and $C'$ is 1; $b(B')$ is 1.1 to 3 times the amount of $a(A') + c(C')$.

14. A polymer product of claim 13 produced in the presence of a solvent.

15. A process for the manufacture of a polymer reaction product containing a plurality of units of the formula

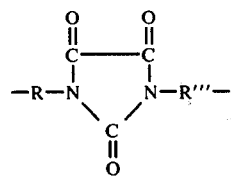 (I)

together with more than one unit selected from the group consisting of

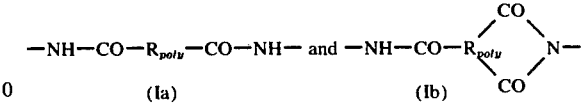

and

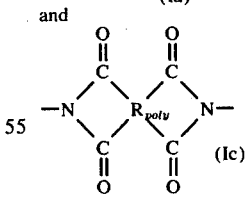

which comprises reacting at a temperature from minus 20° to plus 280° C a. at least one oxamidic ester of Formula VII,

 (VII)

b. at least one isocyanate of Formula VIII

 (VII)

on compound forming an isocyanate under the aforesaid reaction conditions and c. a polycarboxylic acid of Formula $R_{poly}$ (COOH)$_p$ (XXXXV) so as to obtain a condensation product processing amide or imide groups, wherein R is a member selected from the group consisting of aa. an at least mono-nuclear di- to hexavalent aromatic radical having 6 to 18 carbon atoms, bb. an at least mono-nuclear di- to hexavalent heterocyclic radical having 5 to 12 carbon atoms, cc. a radical as defined in aa) being substituted by at most two substituents, selected from the group consisting of halogen, nitro, dialkylamino, diarylamino, alkyl-aryl-amino groups, alkyl, alkoxy, carboxyalkyl, carboxyaryl acyl, cycloalkyl, halogenated alkyl, halogenated alkoxy, halogenated carboxyalkyl, halogenated carbxyaryl or halogenated acyl groups with up to 18 carbon atoms, dd. a radical as defined in bb) being substituted by a substituent selected from the group consisting of halogen, nitro, dialkylamino, diarylamino, alkylarylamino groups, alkyl, alkoxy, carboxyalkyl, carboxyaryl, acyl, cycloalkyl, halogenated alkyl, halogenated alkoxy, halogenated carboxyalkyl, halogenated carboxyaryl and halogenated acyl groups with up to 18 carbon atoms, ee. a quinonyl radical; $R^V$ is an aliphatic hydrocarbon group having up to 18 carbon atoms, a cycloaliphatic hydrocarbon group with up to 8 carbon atoms, an unsubstituted mononuclear aromatic hydrocarbon group or a mononuclear aromatic hydrocarbon having one or more hydrocarbon substituents, said substituents having a total of up to 14 carbon atoms, $R'''$ is a member selected from the group consisting of d1. an at least mono-cyclic di- to tetravalent carboxylic radical having 6 to 30 carbon atoms, e1. an at least mono-cyclic di- to tetravalent heterocyclic radical having 6 to 40 carbon atoms, f1. a radical (d1) being substituted by at least one of the groups halogen, nitro, alkyl, alkoxy, carboxyalkyl, carboxyaryl, acyl, cycloalkyl, halogenated alkyl, halogenated alkoxy, halogenated carboxyalkyl, halogenated carboxyaryl and a halogenated acyl with up to 18 carbon atoms, g1. a radical as defined in e1) being substituted by at least one of the groups halogen, nitro, alkyl, alkoxy, carboxyalkyl, carboxyaryl, acyl, cycloalkyl, halogenated alkyl, halogenated alkoxy, halogenated carboxyalkyl, halogenated carboxyaryl and halogenated acyl with up to 18 carbon atoms, h1. an aliphatic radical with 1 to 20 carbon atoms;

$R_{poly}$ is a member selected from the group consisting of i1. an unsubstituted di- to hexavalent at least monocyclic radical having 6 to 34 carbon atoms, k1. an at least mono-nuclear carboxylic radical having 6 to 34 carbon atoms being substituted by halogen, amino or alkyl groups having a total of 1 to 8 carbon atoms, l1. an aliphatic di- to hexavalent hydrocarbon radical having 2 to 12 carbon atoms and which may have at least one double bond, m1. a heterocyclic radical having 4 to 69 carbon atoms o1. an aliphatic radical (l1) being substituted by alkyl, halogen or amino groups, p1. a heterocyclic radical m1) being substituted by alkyl, halogen or amino groups, r is an integer from 2 to 6 s is an integer from 2 to 4 and p is an integer from 2 to 6 and wherein 1 to r mols of oxamidic ester are reacted with 1 mol of isocyanate or 1 to s mols of isocyanate are reacted with 1 mol of oxamidic ester with the provision that I. more than $1/r$ of the groups of the oxamidic ester (a) are removed by reaction with the isocyanate groups when an excess of ester groups of the oxamidic ester, referred to the isocyanate groups, is used as starting material and that II. more than $1/s$ of the isocyanate groups of the isocyanate (b) are reacted, when an excess of isocyanate groups, referred to the ester groups of the oxamidic ester, is used as a starting material, and III. in which reaction product at least two ester groups of the oxamidic ester are reacted, where an excess or equimolar amount of isocyanate is used, and at least two isocyanate groups are reacted where an excess or equimolar amount of ester groups of the oxamidic ester is used, and IV. wherein components (a) and (c) are reacted in a molar proportion of $(A')$ (0.97 to 0.03) to $(C')$ (0.03 to 0.97) wherein the total of both components is always one mol provided the oxamidic ester and the polycarboxylic acid have the same functionality and wherein the molar proportion of the reaction components is $[(a.A' + c.C') : (b.B')]$ $a(A') + c(C') = b(B')$ wherein a is the number of oxamidic ester groups in said A' mols of oxamidic ester, b is the number of isocyanate groups in said B' mols of isocyanate, c is the number of the carboxylic groups in C' mols of poly-carboxylic acid and a and b are integers of from 2 to 4 and c is an integer from 2 to 6 and wherein $[(b.B')]$ $b(B')$ is up to three times the amount of $[(a.A' + c.C')]$ $a(A') + c(C')$.

16. A process as claimed in claim 15 wherein the reaction is performed in a melt or in the presence of a solvent.

17. A process as claimed in claim 15 wherein the reaction is performed in the presence of an amine, phosphine or an alcoholate or an organic tin or lithium compound or of a mixture of such compounds as a catalyst.

18. A process as claimed in claim 15 wherein the polycarboxylic acid component is trimellitic anhydride.

19. A process as claimed in claim 15 wherein the isocyanate is 4,4' diisocyanato-diphenylmethane.

20. A process as claimed in claim 15 wherein the oxamidic ester is 4,4' bis (ethoxalylamino)-diphenylmethane.

21. A process as claimed in claim 15 wherein the isocyanate is 4,4' diisocyanato-diphenyl methane and the polycarboxylic acid component is trimellitic anhydride.

22. A process as claimed in claim 15 wherein the isocyanate is 4,4' diisocyanato-diphenyl methane and the oxamidic ester is 4,4' bis (ethoxalylamino) diphenylmethane.

23. A process as claimed in claim 15 wherein the polycarboxylic acid component is trimellitic anhydride and the oxamidic ester is 4,4' bis (ethoxalylamino) diphenylmethane.

* * * * *